United States Patent

Poliakoff et al.

(10) Patent No.: US 6,566,558 B1
(45) Date of Patent: May 20, 2003

(54) HYDROFORMYLATION REACTIONS

(75) Inventors: Martyn Poliakoff, Nottingham (GB); Nicola J. Meehan, Nottingham (GB); Stephen K. Ross, County Durham (GB); Stefan Wieland, Offenbach (DE); Stefan Roeder, Frankfurt am Main (DE)

(73) Assignee: Thomas Swan & Co., Limited, County Durham (GB)

( * ) Notice: Subject to any disclaimer, the term of this patent is extended or adjusted under 35 U.S.C. 154(b) by 0 days.

(21) Appl. No.: 09/720,295

(22) PCT Filed: Jun. 30, 1999

(86) PCT No.: PCT/GB99/02058

§ 371 (c)(1),
(2), (4) Date: Mar. 12, 2001

(87) PCT Pub. No.: WO00/01651

PCT Pub. Date: Jan. 13, 2000

(30) Foreign Application Priority Data

Jul. 1, 1998 (GB) .............................................. 9814301
Mar. 1, 1999 (GB) .............................................. 9904603

(51) Int. Cl.[7] .............................................. C07C 45/50
(52) U.S. Cl. ...................................... 568/454; 568/451
(58) Field of Search ................................ 568/451, 454

(56) References Cited

U.S. PATENT DOCUMENTS 5,198,589 A    3/1993  Rathke et al. .............. 568/454

FOREIGN PATENT DOCUMENTS

| WO | WO 97/38955 | 10/1997 | ........... C07B/35/02 |
| WO | WO 00/01651 | 1/2000  | ........... C07C/45/50 |

OTHER PUBLICATIONS

Philip et al, Organometallics, 14(3), 1510–13, 1995.*
Caludio et al, Inorg. Chem., 7(2), 120–3 (1995).*
Krocher et al., Sol–gel hybrid materials as heterogeneous catalysts for the synthesis of N, –dimethylformamide from supercritical carbon dioxide, Department of Chemical Engineering and Industrial Chemistry, Swiss Federal Institute of Technology, ETH–Zentrum, CH–8092 Zurich, Switzerland, p. 1497–1498, Chem. Commun., 1996.

* cited by examiner

*Primary Examiner*—Sreeni Padmanabhan
(74) *Attorney, Agent, or Firm*—Bromberg & Sunstein LLP

(57) ABSTRACT

In a process for the hydroformylation of alkanes, alkenes or trialkylboranes under supercritical or near-critical conditions, hydroformylation is effected using a heterogeneous catalyst in a continuous flow reactor containing a supercritical or near-critical reaction medium. Selectivity of product formation may be achieved by independently varying one of more of the temperature, pressure, catalyst, mole ratios of hydrogen and carbon monoxide and flow rate.

17 Claims, 2 Drawing Sheets

HYDROFORMYLATION REACTIONS

This Application is a 371 of PCT/GB99/02058 filed Jun. 30, 1999.

The present invention relates to a method for carrying out hydroformylation reactions. Specifically the present invention relates to the hydroformylation reactions catalysed by heterogeneous catalysts in near-critical or supercritical fluids.

BACKGROUND

The use of carbon monoxide as a reagent for organic synthesis is diverse with a wide number of reactions carried out. One process of industrial importance is hydroformylation (also known as the "oxo process") which is used for large-scale production of aliphatic aldehydes and alcohols from olefins (alkenes) using cobalt- or rhodium-based homogeneous catalysts.

In general, the hydroformylation reaction involves reaction of an alkene or alkyne with a mixture of carbon monoxide and hydrogen over a catalyst at high pressure to produce a carbonyl compound. Mixtures of hydrogen and carbon monoxide are frequently referred to as synthesis gas or syn gas.

FIG. 1 shows the hydroformylation of an alkene in general terms. The resulting carbonyl compound, which may be the normal (n) or iso product, can then be reduced to give the corresponding alcohol. An alternative route is first to convert the alkene or alkyne to a trialkylborane and then to react this product with carbon monoxide and a reducing agent.

It is well known that reactions of this type are limited by the solubility of the gases in the liquid reagent or solvent (known as Mass Transport Limitations). The use of supercritical fluids in the replacement of conventional solvents for environmental reasons is gradually being adopted. The use of supercritical fluids as reaction media also gives higher solubilities of gases in the system and gives effectively a higher activity of these reagents by overcoming Mass Transport limitations.

Work has previously been carried out on batch systems using homogeneous catalysts in supercritical fluids. The following are examples of known heterogeneous hydroformylation reactions:
1) the Hydroformylation of olefins, Chemtracts: Org. Chem. 1996, 9 (6), 318–321 and Chemtracts: Inorg. Chem. (1995), 7(2), 120–123.
2) The Hydroformylation of Propylene in a batch system using homogeneous catalysis in Supercritical fluids is reported by Akgerman et al (Fourth Italian Conference on Supercritical Fluids and their Applications, September 1997 Proceeding, page 263–269).
3) U.S. Pat. No. 5,198,589 describes a batch or continuous batch process using homogenous catalysis.

However, the use of homogeneous catalysts and batch processes lead to the problems of catalyst separation, long residence time and scale-up hazards. Indeed, it is quite a significant problem with the processes described in these publications that the use of homogeneous catalysts requires a separation step at the end of the process to recover the catalysts, because this necessitates extra processing steps and thus increases costs. Also, separation is particularly difficult in the case of alkenes which have a chain length longer than C7 because separating the catalysts from the products by distillation requires high temperatures which destroy the catalysts. Consequently, these processes involving alkenes having a chain length greater than C7 cannot be carried out in continuous-flow reactors (tubular reactors).

The use of homogeneous catalysts also means that these processes are usually carried out in batch or semi-batch reactors. Such conditions require extensive capital expenditure when scaling up owing to the design requirement for vessels capable of working at high pressure. The use of batch systems also has the disadvantage of increased down time for charging and discharging the reaction vessel. There is also the problem that the product of the reaction may be a mixture of thermodynamic and kinetic products, owing to the large residence time of the reactants in the reactor.

Work has been carried out in the past on heterogeneous catalysis for hydroformylations under conventional (i.e. not near-critical or supercritical conditions). However, these reactions have never proved successful, usually because of low conversion to the products and catalyst deactivation. Heterogeneous catalysed hydroformylation reactions carried out in supercritical media have not previously been reported. As a result, hydroformylation reactions cannot presently be carried out using a heterogenous catalyst on an industrial scale.

There is thus a need for a hydroformylation process in which the catalyst can be easily separated from the product by simple filtration. Ideally, the process should enable separation to be achieved even for hydroformylations of alkenes, alkynes or trialkylboranes having chain lengths greater than C7.

There is also a requirement for a hydroformylation process in which a continuous flow reactor (tubular reactor) can be used. Ideally, the process should allow the operator the ability to control residence time as well as the other reaction parameters independently in order to allow greater control of the reaction. There is also a need for a process which is more efficient and/or more selective than conventional processes.

Surprisingly, we have found that hydroformylation of alkenes, alkynes and trialkylboranes can be effected using a heterogenous catalyst in supercritical media. Thus, by using a combination of a supercritical medium, comprising one or more components, and a heterogeneous catalyst (e.g. the Deloxan HK1 2% rhodium complex catalyst from Degussa) it is possible to carry out hydroformylation reactions with high conversion. It is also possible to perform the reaction with good selectivity for the n or iso products where there is the possibility of forming both the normal and iso products. The present invention thus solves the problems of the prior art by effecting the hydroformylation reaction under conditions close to or above the supercritical point of the reaction medium in the presence of a heterogeneous catalyst in a continuous flow reactor.

According to the present invention, there is provided a process for hydroformylation of a substrate, wherein the substrate is selected from alkenes, alkynes, and trialkylboranes and is reacted with hydrogen and carbon monoxide in the presence of a heterogeneous catalyst, the substrate being a fluid in its supercritical or near-critical state and/or, reaction taking place in the presence of a solvent for the substrate, the solvent being in its supercritical or rear-critical state, and the process being carried out in a continuous flow reactor. The yield and/or selectivity of the reaction may be influenced by controlling one or more of the reaction conditions of temperature, pressure, residence time, flow rate and catalyst.

In an embodiment, the catalyst comprises a support selected from: an organosiloxane-polycondensate, an organosiloxane-copolycondensate, or polymeric secondary and/or tertiary organosiloxanamine combinations; and a metal or metal complex in which the metal is selected from: platinum, nickel, palladium, cobalt, rhodium, iridium, iron, ruthenium, and osmium, and the catalyst optionally includes a promoter. Rhodium is a particularly preferred metal.

Suitable catalysts thus include Deloxan HK1 which is a 2% Rh catalyst on a polyaminosiloxane support obtainable from Degussa.

The hydroformylation reaction of the present invention satisfies the above requirements by providing a process in which the products can be separated from the catalyst after reaction without difficulty. This is true for reactions on alkenes, alkynes or trialkylboranes having a chain length greater than C7. Hence alkenes, alkynes or trialkylboranes having a chain length greater than C7 can be hydroformylated and the products easily separated from the catalyst without the need for distillation or further work-up.

The process also results in yields and selectivities which are better than conventional processes. In particular, the feature of selectivity is an important feature of the invention because the iso product is frequently a by-product of hydroformylation reactions carried out under conventional conditions in cases where the production of both normal and iso-compounds is possible. Thus, the process of the present invention can substantially reduce the incidence of the iso product if this is desirable. In some circumstances the iso product may be the desired product, in which case the reaction conditions may be optimised for the iso product.

The process of the present invention also enables the reaction to be carried out in a tubular reactor. The use of a tubular reactor has the advantage of having a low inventory of reagents under high pressure at any moment hence increasing the overall safety of the process.

Furthermore, we have also found that under such conditions the reactor can be made very efficient using only half the amount of syn gas which is required by Akgerman et al. in the reported process. Surprisingly, alteration of the pressure in the reactor gives selectivity with regard to the ratio of n to iso products (this can be seen from Table 1 given later with Example 1). Thus, by varying the pressure of the supercritical medium it is possible to achieve ratios greater than 3:1 of the n:iso products.

In the process of the present invention at least one of the components, other than the hydrogen or carbon monoxide, is under supercritical or near-critical conditions. One or more of temperature, pressure, flow rates, and hydrogen and carbon monoxide concentration may be independently controlled for a given catalyst so as to influence the selectivity of the reaction. The catalyst may also be varied (either for a given set of conditions or under various conditions of temperature, pressure, flow rate etc.) to influence the yield and/or selectivity of the product.

The alkene, alkyne or trialkylborane substrate is hydroformylated in a continuous process which preferably comprises the steps of:

(a) admixing a supply of an inert fluid as solvent with a supply of the substrate and a supply of hydrogen and carbon monoxide at pre-determined flow rates;

(b) adjusting the temperature and pressure of the resulting admixture to pre-determined values of temperature and pressure close to or above the critical point of a fluid present in the reaction system and exclusive of CO and $H_2$ to produce a reaction mixture from which the desired carbonyl product is formed as the major carbonyl product, wherein the choice of the pre-determined values of temperature and pressure is dependent on which of the possible hydroformylation products is to be formed;

(c) exposing the reaction mixture to a heterogeneous catalyst to facilitate reaction; and (d) removing the reaction mixture after reaction from the region of the catalyst and isolating the desired product by depressurisation of the reaction mixture.

The heterogeneous continuous flow system of the present invention offers a number of advantages compared with batch type systems or a homogenous continuous flow system. In particular, the present invention allows the formation of a desired end product in good yield and/or a selective manner by controlling one or more of: the temperature, the pressure of the reaction, by varying the catalyst used for a given set of reagents, the flow rate through the apparatus, and the mole ratios of the hydrogen and carbon monoxide to is the substrate.

The factors controlling the selectivity of hydroformylation will depend on the particular reaction and in some instances the temperature or the pressure will be the controlling factor, whereas in other cases the catalyst or flow rate may be more important in determining the outcome of the reaction. Suitable conditions for a given substrate and desired product are thus determined in accordance with the present invention.

The present invention also offers the advantage that hazardous reagents may be used without the need for a high inventory of reagent at any one time, since the organic compound and the hydrogen and carbon monoxide are continuously fed to the reactor.

Similarly, the reaction product or products are collected continuously from the reactor and do not therefore accumulate in large quantities in the reactor. This has the further advantage that the products are less likely to suffer degradation. There is also a concomitant increase in the safety of the process as compared to a batch-process when using hazardous reagents or when forming hazardous products since these materials are not usually present in sufficient quantities to represent a significant risk. Since the continuous flow process of the present invention also allows cleaner reactions to be performed than those of a corresponding batch-type process, the cost of purifying the products is reduced.

The present invention has the further advantage of providing higher yields and higher throughputs than conventional methods in some cases. Whilst the actual throughputs will inevitably depend on the particular reaction employed and the size of the apparatus, throughputs of 25 mls per minute or higher are attainable using laboratory scale apparatus. Furthermore, selectivities in excess of 3 to 1 in favour of the normal carbonyl product can easily be achieved using the process of the present invention.

The hydroformylation reaction of the present invention is performed close to or above supercritical point of the desired medium. Any fluid having a supercritical point may be employed for the process of the present invention provided that it is compatible with the reactants. In addition, the alkene, alkyne or trialkylborane (if it is not a solid). may be both the substrate and the supercritical medium. However, in practice the choice of fluid will depend upon the solubility of the substrate in the fluid since a function of the super-critical or near-critical fluid is to act as a solvent for the substrate and the hydrogen and carbon monoxide. It is also important that the reaction medium is inert with respect to the reactants and the products of the reaction in order to avoid undesirable side reactions. Particularly favoured media include carbon dioxide, sulphur dioxide, alkanes such as ethane, propane and butane, and saturated halocarbons such as trichlorofluoromethane, dichlorofluoromethane, dichlorodifluoromethane, chlorotrifluoromethane, bromotrifluoromethane, trifluoromethane, and hexafluoroethane. The reaction medium may be a mixture of two or more fluids having critical points which do not require commercially unacceptable conditions of temperature and pressure in order to achieve the necessary conditions for reaction according to the present invention. For example, mixtures of carbon dioxide with an alkane such as ethane or propane, or a mixture of carbon dioxide and sulphur dioxide may be employed close to or above their theoretical critical points.

In the context of the present invention, the lower limit of the conditions suitable for supporting the hydroformylation reaction are conditions of temperature and pressure below but near the critical point. When a fluid reaches its critical point its density is substantially decreased relative to its density at its boiling point at normal pressure. Small changes in pressure near the critical point cause additional changes in density. The process will operate in the fluid at temperatures and pressures below the critical point but at which the density of the fluid is sufficient to ensure that the substrate and the hydrogen and carbon monoxide are substantially in a single phase. The upper limit of temperature and pressure is governed by limitations of the apparatus.

Although aliphatic compounds are more difficult to hydroformylate than aromatic compounds under the reaction conditions employed in the present invention, the hydroformylation of both aliphatic and aromatic compounds is possible according to the present invention.

Product formation may be monitored in situ by means of IR spectrometry using a suitably positioned high pressure IR cell, or by gas chromatography (GC) performed on samples withdrawn from the reactor.

The present invention will now be described by way of example only with reference to the Figures in which:

Figure 1:
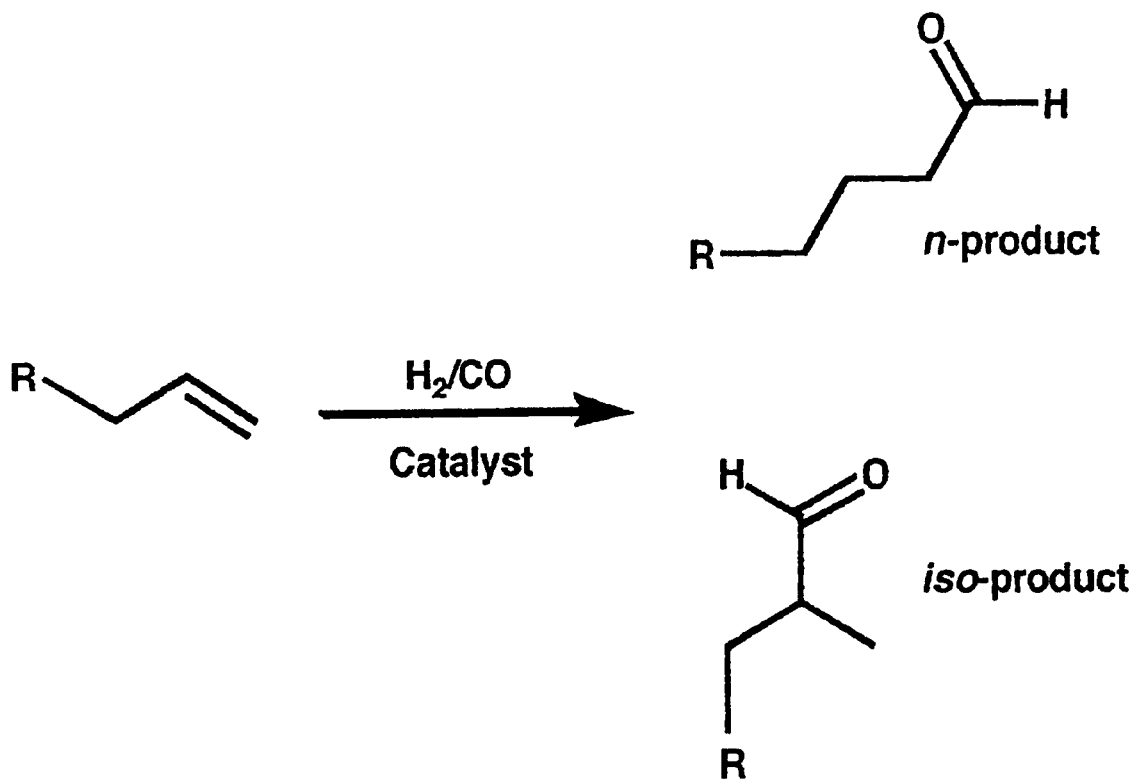
FIG. 1 is a schematic diagram of a hydroformylation reaction.
Figure 2:
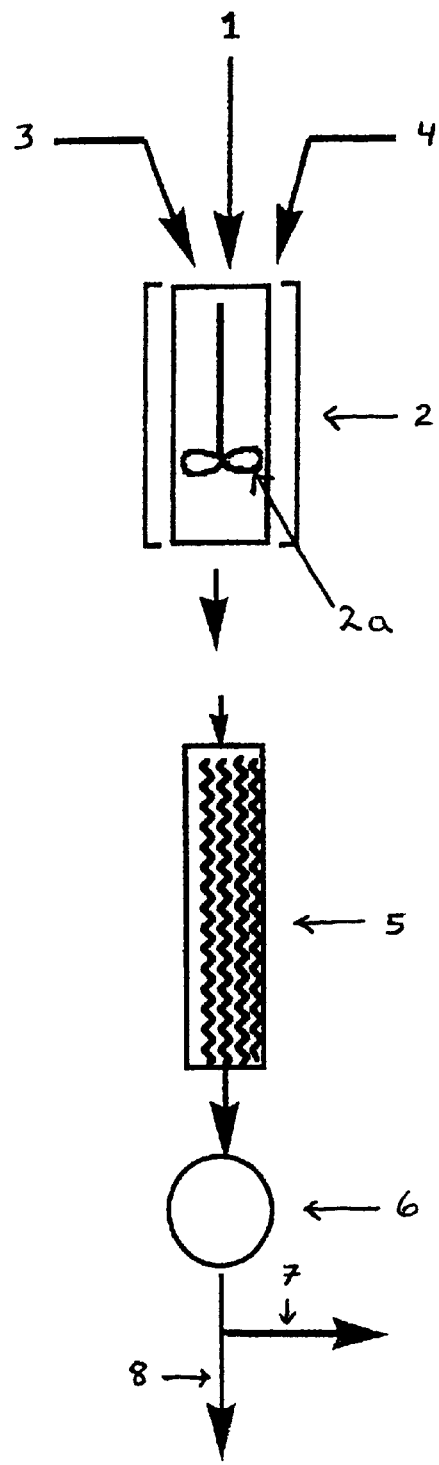
FIG. 2 is a schematic diagram of a continuous flow reactor according to the present invention.

The substrate 1, dissolved in an appropriate solvent if it is a solid, is pumped into mixer 2 which may include a stirrer 2a where it is mixed with fluid 3 which has been delivered from a reservoir via a pump to mixer 2. Mixing of substrate 1 and fluid 3 may equally be effected without the use of a stirrer. Hydrogen and carbon monoxide in the form of mixture 4 is delivered from a reservoir via a compressor and a dosage unit (e.g. an injection valve) to mixer 2. The ratios of the hydrogen and carbon monoxide may be independently varied as required. The hydrogen/carbon monoxide mixture 4 has a pressure of typically 200 to 220 bar, inclusive. This pressure is obtained by means of conventional pressure regulating apparatus. Addition of dissolved substrate 1 and/or mixture 4 may be continuous or may occur continuously in a step-wise manner. The hydrogen/carbon monoxide mixture 4 is added via a switching valve or similar control means to give the required ratio of the mixture 4 to the substrate 1. The ratio of hydrogen and carbon monoxide to substrate is chosen according to the reaction to be used and is typically in the range from 1.0:1.0, to 3.0:1.0, inclusive, equivalents of syn gas (i.e. the mixture 4) per reaction.

The temperature and/or pressure of the mixture of substrate 1, fluid 3 and the hydrogen/carbon monoxide mixture 4 is adjusted in mixer 2 to a temperature and pressure close to or above the critical point of fluid 3 as required. Heating means or cooling means are provided in mixer 2 for this purpose. The mixture is then passed into reactor 5 which contains a catalyst (not shown) fixed on a suitable support.

After an appropriate residence time in reactor 5 fluid 3, which contains the product is passed into pressure reduction unit 6 and the products 7 are removed via take a off tap after passing through pressure reduction unit 6. The flow rate of the reactants through reactor 5 is controlled by a valve (not shown) in pressure reducer 6. The quantity of materials consumed in the reaction and the rate of reaction are determined by the temperature, the feed rate of substrate 1 into fluid 3 and the flow rate of fluid 3. Fluid 3, together with any unconsumed hydrogen and carbon monoxide, is vented through a relief pipe 8 for subsequent recycling or disposal.

The parameters of a typical reaction might involve a system pressure of 60 to 140 bar (this will, of course, depend in part on the reaction media), a flow rate of the substrate of 0.5 to 20.0 ml/min, a reactor temperature of 40 to 360° C. (again, this will depend in part on the reaction media) and a flow rate of the supercritical or near critical fluid of 0.65 to 1.65 l/min; however, these parameters do not imply limitations to within the respective ranges.

EXAMPLE 1

Oct-1-ene is pumped at 0.5 ml/min into a heated mixer which may include a stirrer where it is mixed with synthesis gas (syn gas). The supercritical reaction medium is carbon dioxide and the system pressure is set via a pressure regulator on the carbon dioxide inlet. The reactor is set at the appropriate temperature (see Table 1) and the mixture is passed through the reactor containing the heterogeneous catalyst (Deloxan HK1, ex Degussa). After reaction, the pressure is dropped via a two-stage expansion valve through which the gaseous carbon dioxide is vented and the products are collected. The results obtained in this reaction under various conditions are shown in Table 1, with analysis of the products being carried out by GC using normalised areas.

It is apparent from Table 1 that for a given reaction medium, variation of the temperature and ratio of substrate to hydrogen and carbon monoxide (syn gas) allows control of the ratio of normal to iso carbonyl product.

TABLE 1

| Reactor Temp/° C. | Pressure Bar | Molar Equivalents of Syn gas | Reactor Volume/ml | Conversion/ % | Yield of Aldehydes/ % (Nonanal) | n:iso Ratio | Flowrate of $CO_2/(1/min)$ |
|---|---|---|---|---|---|---|---|
| 150 | 100 | 1.5 | 5 | 89.6 | 55.6 | 2.4:1 | 0.65 |
| 150 | 120 | 1.1 | 5 | 73.7 | 41.3 | 1.7:1 | 0.65 |
| 150 | 120 | 1.5 | 5 | 94.5 | 64.7 | 2.9:1 | 0.65 |
| 150 | 120 | 1.9 | 5 | 96.4 | 70.5 | 3.5:1 | 0.65 |
| 150 | 140 | 1.5 | 5 | 94.3 | 79.2 | 1.9:1 | 0.65 |
| 100 | 120 | 3.0 | 10 | 93.0 | 78.0 | 1.7:1 | 0.65 |

What is claimed is:

1. A process for the continuous hydroformylation of a substrate, wherein the substrate is selected from alkenes, alkynes, and trialkylboranes and is reacted with hydrogen and carbon monoxide in the presence of a heterogeneous catalyst, the substrate being a fluid in its supercritical or near-critical state and/or, the reaction taking place in the presence of a solvent for the substrate, the solvent being in its supercritical or near-critical state, and the process being carried out in a continuous flow reactor.

2. A process according to claim 1, which comprises controlling one or more of the reaction conditions of temperature, pressure, residence time, flow rate and catalyst so as to influence the yield and/or selectivity of the reaction.

3. A process according to claim 1 or 2, wherein a solvent is present which is one or more of: carbon dioxide, an alkane, ammonia, nitrogen and a saturated halocarbon.

4. A process according to claim 1, 2 or 3, wherein the catalyst is a supported metal catalyst.

5. A process according to claim 4, wherein the catalyst comprises:
- a support selected from an organosiloxane-polycondensate, an organosiloxane-co-polycondensate, and polymeric secondary and/or tertiary organosiloxanamine combinations; and
- a metal or metal complex in which the metal or metal portion of the metal complex is selected from platinum, nickel, palladium, cobalt, rhodium, iridium, iron, ruthenium, and osmium.

6. A process according to claim 5, wherein the catalyst further comprises:
- a promoter.

7. A process for hydroformylation of a substrate, wherein the substrate is selected from alkenes, alkynes, and trialkylboranes and is reacted with hydrogen and carbon monoxide in the presence of a heterogeneous catalyst and an additional solvent being in a supercritical or near-critical state, and wherein one or more of the reaction conditions of temperature, pressure, residence time, flow rate and catalyst may be controlled so as to influence the yield and/or selectivity of the reaction.

8. A process according to claim 7, wherein the process is carried out in a continuous flow reactor.

9. A process according to claim 7, wherein the additional solvent is selected from carbon dioxide, an alkane, ammonia, nitrogen, a saturated halocarbon, the substrate and combinations thereof.

10. A process according to claim 7, wherein the catalyst is a supported metal catalyst.

11. A process according to claim 10, wherein the catalyst comprises:
- a support selected from an organosiloxane-polycondensate, an organosiloxane-co-polycondensate, and polymeric secondary and/or tertiary organosiloxanamine combinations; and
- a metal or metal complex in which the metal or metal portion of the metal complex is selected from platinum, nickel, palladium, cobalt, rhodium, iridium, iron, ruthenium and osmium.

12. A process according to claim 11, wherein the catalyst further comprises:
- a promoter.

13. A process for hydroformylation of a substrate, wherein the substrate is selected from alkenes, alkynes, and trialkylboranes, the substrate being a fluid in a supercritical or near-critical state, the process carried out in a continuous flow reactor, the process comprising:
reacting the substrate with hydrogen and carbon monoxide in the presence of a heterogeneous catalyst.

14. A process according to claim 13, further comprising:
controlling one or more reaction conditions, the reaction conditions including temperature, pressure, residence time, flow rate and the catalyst, so as to influence the yield and/or selectivity of reaction.

15. A process according to claim 14, wherein, in reacting, the catalyst is a supported metal catalyst.

16. A process according to claim 15, wherein, in reacting, the catalyst comprises:
- a support selected from an organosiloxane-polycondensate, an organosiloxane-co-polycondensate, and polymeric secondary and/or tertiary organosiloxanamine combinations; and
- a metal or metal complex in which the metal or metal portion of the metal complex is selected from platinum, nickel, palladium, cobalt, rhodium, iridium, iron, ruthenium and osmium.

17. A process according to claim 16, wherein, in reacting, the catalyst further comprises:
- a promoter.

* * * * *